United States Patent [19]

Ogura

[11] Patent Number: 4,787,394
[45] Date of Patent: Nov. 29, 1988

[54] ULTRASOUND THERAPY APPARATUS

[75] Inventor: Ichiro Ogura, Yokohama, Japan

[73] Assignee: Kabushiki Kaisha Toshiba, Kawasaki, Japan

[21] Appl. No.: 41,423

[22] Filed: Apr. 23, 1987

[30] Foreign Application Priority Data

Apr. 24, 1986 [JP] Japan ................................. 61-95416

[51] Int. Cl.$^4$ ............................................. A61B 10/00
[52] U.S. Cl. ............................. 128/660.03; 128/24 A
[58] Field of Search ................. 128/24 A, 328, 660, 128/804, 663; 367/141, 142, 154

[56] References Cited

U.S. PATENT DOCUMENTS

| | | | |
|---|---|---|---|
| 4,416,286 | 11/1983 | Iinuma et al. | 128/663 |
| 4,510,277 | 2/1985 | Hongo | 128/660 |
| 4,543,959 | 10/1985 | Sepponen | 128/660 X |
| 4,610,249 | 9/1986 | Makofski et al. | 128/328 |
| 4,658,828 | 4/1987 | Dory | 128/660 |
| 4,669,483 | 6/1987 | Hepp et al. | 128/660 |
| 4,696,299 | 9/1987 | Shene et al. | 128/328 |

FOREIGN PATENT DOCUMENTS

| | | | |
|---|---|---|---|
| 0168559 | 1/1986 | European Pat. Off. | 128/328 |
| 59-101143 | 11/1984 | Japan | 128/660.01 |

*Primary Examiner*—Ruth S. Smith
*Attorney, Agent, or Firm*—Oblon, Fisher, Spivak, McClelland, & Maier

[57] ABSTRACT

An ultrasound therapy apparatus having an applicator. The applicator comprises at least one ultrasonic beam emitter, at least two ultrasonic transducers, and a support member. The beam emitter emits an ultrasonic beam onto an object within a patient, for the purpose of treating the object. The transducers apply ultrasonic beams to the patient and detect ultrasonic echoes coming from the patient, thereby to form two tomograms, each of a selected plane of the patient, one plane intersecting with the other on a line passing through a region in which the beam emitted by the beam emitter is focused. The support member supports the beam emitter and the transducers in a specific positional relationship. Receivers receive echo signals corresponding to the ultrasonic echoes. Two displays display tomograms formed from these echo signals. They also display a first marker, which indicates a region in which the ultrasonic beam emitted from the beam emitter is focused, and also a second marker, which represents an intersection line of the two planes. By referring to these markers, an operator can set the applicator in a position whereby the beam emitted from the beam emitter is focused onto the object.

6 Claims, 4 Drawing Sheets

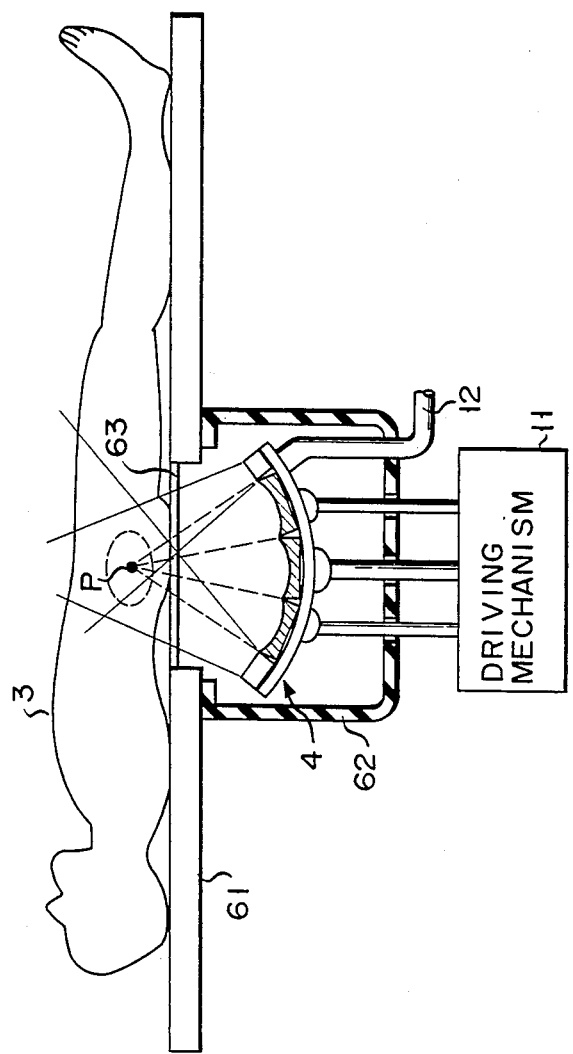

ULTRASOUND THERAPY APPARATUS

BACKGROUND OF THE INVENTION

1. Field of the Invention

The present invention relates to an ultrasound therapy apparatus for applying an ultrasonic beam to a calculus or a tumor, and more particularly, to an apparatus for displaying a tomogram of a region of interest (ROI) of a patient, and for setting, with reference to the tomogram, an applicator (e.g., an ultrasonic beam emitter) in such a position that the beam emitted therefrom is precisely focused on the calculus or tumor present in the ROI.

2. Discussion of Background

With a therapy apparatus for applying an ultrasonic beam to disintegrate a calculus, it is necessary to focus the beam exactly on the calculus in order to effectively disintegrate it without damaging the tissues in the close vicinity thereof. Hence, the applicator for emitting the beam must be set in such a position that the beam emitted is sharply focused on the calculus itself. To correctly position the applicator, a tomogram of the ROI must be displayed to help a doctor ascertain the exact location of the calculus.

Japanese Patent Disclosure (Kokai) No. 59-101143 discloses a therapy apparatus comprising an ultrasonic beam emitter and two ultrasonic transducers. The beam emitter emits an ultrasonic beam to disintegrate a calculus. The transducers are used to form and display, in two selected, intersecting planes, the images of the region of interest. By examining these images (i.e., the two tomograms), the doctor can ascertain the precise location of the calculus. However, since the operator cannot clearly determine the exact location at which the emitted beam is focused, he or she cannot move the beam emitter to ensure that the ultrasonic beam is sharply focused on the calculus.

European Patent Publication No. 0148653 discloses an ultrasound therapy apparatus comprising a main piezoelectric transducer with an auxiliary piezoelectric transducer secured thereto. The main transducer is used to emit an ultrasonic beam for disintegrating a calculus, and the auxiliary transducer is provided to form a tomogram of the ROI in which the calculus has been found. The main transducer is supported by a support device which is used to move the main transducer along the X, Y, and Z axes which intersect with one another at the right angles. The apparatus further comprises a display device for displaying the tomogram and a cross for indicating the theoretical focal point of the main piezoelectric transducer. The operator operates the support device in the X direction, thus moving the main transducer in the X direction until the cross appears on the screen of the display device. Then, he or she operates the support device in the Y and Z directions, thereby moving the main transducer in the Y and Z directions until the cross is positioned at the center of the image of the calculus displayed on the screen. In this way, the main piezoelectric transducer can be set at its optimum position.

Even so, it is time-consuming to move the image of the calculus into the field of view of the auxiliary piezoelectric transducer, for the two reasons.

First, the display device displays only one tomogram.

Secondly, the calculus moves as the patient breathes or moves.

Further, since only one tomogram is displayed, the operator cannot visualize a stereoscopic image of the calculus, and thus cannot know with certainty whether or not the calculus has been throughly disintegrated. In most cases, a calculus is not crushed to the same extent in all directions when an ultrasonic beam is applied to it. Accordingly, even if one tomogram of the ROI suggests that the calculus has been disintegrated to a sufficient extent in one direction, it may not have been disintegrated to the same extent in another direction. In this case, the doctor may mistakenly believe that the calculus has been completely disintegrated and thus may take no further remedial action.

SUMMARY OF THE INVENTION

It is accordingly an object of this invention to provide an ultrasound therapy apparatus which enables an operator to positively focus an ultrasonic beam onto an object, such as a calculus, which is present in a region of interest of a patient, and to visualize a stereoscopic image of this object.

The above object can be attained by an apparatus which comprises:

at least one ultrasonic beam emitter for emitting an ultrasonic beam onto an object within a patient, for the purpose of treating the object;

at least two ultrasonic transducers for applying ultrasonic beams to the patient and detecting ultrasonic echoes coming from the patient, thereby to form two tomograms, each of a selected plane of the patient, one plane intersecting with the other on a line which passes through a region in which the beam emitted by the ultrasonic beam emitter is focused;

a support member for supporting the ultrasonic beam emitter and the ultrasonic transducers in a specific positional relationship;

means for mechanically driving the support member such that the beam emitted from the ultrasonic beam emitter is focused at a given position within the patient;

means for supplying drive signals to the ultrasonic beam emitter;

signal-transmitting means for supplying drive signals to the ultrasonic transducers during the period when no drive signals are supplied to the ultrasonic beam emitter;

signal-receiving means for receiving echo signals corresponding to the ultrasonic echoes detected by the ultrasonic transducers; and display means for displaying tomograms formed by the ultrasonic transducers, in accordance with the echo signals supplied from the signal-receiving means, and for displaying a first marker, indicating a region in which the ultrasonic beam emitted from the ultrasonic beam emitter is focused, and also a second marker, representing an intersection line of the two planes.

The support member is mechanically driven until either tomogram overlaps the first marker, thereby setting the ultrasonic beam emitter in such a position that the beam emitted from the beam emitter is focused on the object to be medically treated. More precisely, this positioning is performed in the following way:

First, the support member is driven, thus moving the two tomograms until they overlap the second marker, which represents the intersection line. Then, the support member is driven, while holding the tomograms in the overlapping conditions, thereby moving the image of the object along the second marker until the image overlaps the first marker. In this way, the display means displays two tomograms simultaneously. This enables an operator to visualize a stereoscopic image of the object.

BRIEF DESCRIPTION OF THE DRAWINGS

FIG. 6 shows the major components of yet another embodiment of the present invention.

DETAILED DESCRIPTION OF THE PREFERRED EMBODIMENTS

Figure 1:
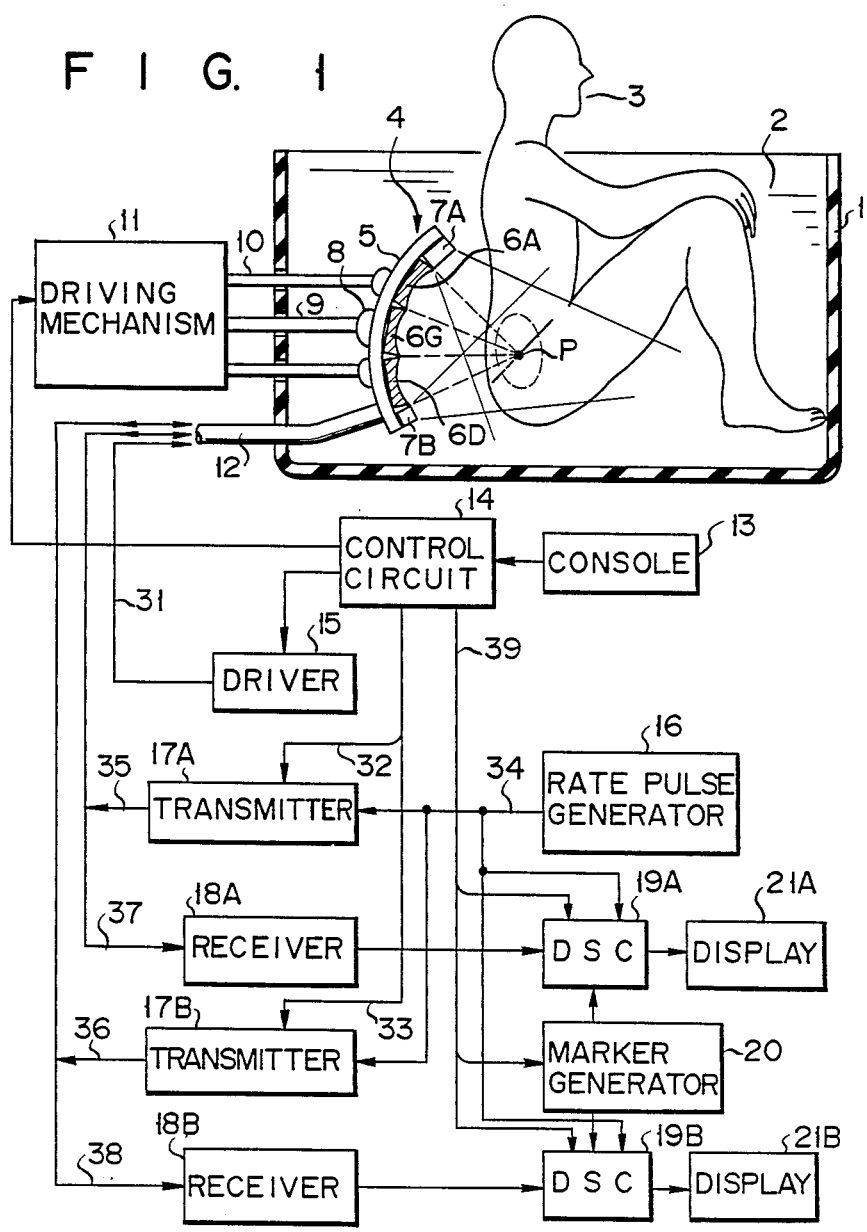
FIG. 1 is a block diagram showing a calculus crusher, which is a first embodiment of the present invention.
Figure 2:
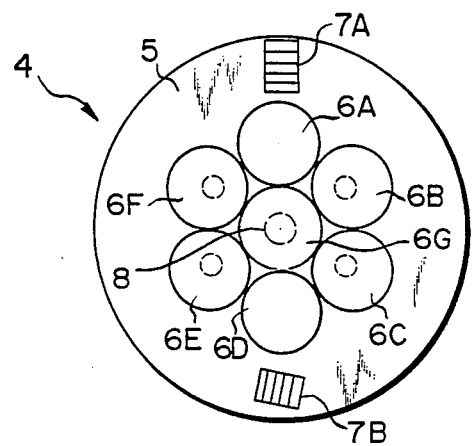
FIG. 2 is a front view of the applicator used in the calculus crusher of FIG. 1.

FIG. 1 shows a first embodiment of this invention. Patient 3 having a calculus in his or her kidney sits in bathtub 1 filled with water 2. Applicator 4 is immersed in bathtub 1. As is shown in FIGS. 1 and 2, applicator 4 comprises support disk 5, even ultrasonic beam emitters 6A to 6G, and two ultrasonic transducers 7A and 7B. Support disk 5 has a diameter of about 350 mm and a spherically concave surface.

Beam emitters 6A to 6G are secured to the spherically concave surface of disk 5 and designed to emit ultrasonic beams for disintegrating the calculus. They are circular piezoelectric elements having a diameter of about 100 mm, and arranged such that the ultrasonic beams emitted from them are focused at one point. They can be replaced by annular array of piezoelectric elements, by a phased array of piezoelectric elements, or by a unit consisting of piezoelectric elements and an acoustic lens for focusing the ultrasonic beams emitted from these elements.

Ultrasonic transducers 7A and 7B are secured also to the spherically concave surface of disk 5 and used to form two tomograms of the ROI of patient 3. Each of transducers 7A and 7B has an array of piezoelectric elements, which is of the same type commonly used in an ultrasonic diagnosis apparatus to form a B-mode tomogram. Both transducers 7A and 7B emit ultrasonic beams to the ROI of patient 3, and detects ultrasonic echoes from the ROI, thereby forming two tomograms of two planes in patient 3 intersecting with each other on a line which passes through a region in which the beams emitted by applicator 4 are focused. As is shown in FIG. 2, ultrasonic transducers 7A and 7B are located outside the region where beam emitters 6A to 6C are provided and are diametrically opposite to each other. Transducers 7A and 7B are so positioned that the axis of the piezoelectric element array of transducer 7A is inclined at a predetermined angle to the axis of the piezoelectric element array of transducer 7B.

Support disk 5 supports ultrasonic beam emitters 6A to 6G and ultrasonic transducers 7A and 7B in such specific positional relationship as has been described. The center of disk 5 is coupled by universal joint 8 (e.g., a ball-and-cup joint) to the distal end of shaft 9. Further, four edge portions of disk 5 are coupled by universal joints to the distal ends of four shafts 10. Shafts 9 and 10 are connected at the proximal end to driving mechanism 11. Driving mechanism 11 moves shafts 9 and 10 in their axial directions, thereby setting support disk 5 in such a position that the ultrasonic beams emitted from emitters 6A to 6G are focused at a desired point within the ROI of patient 3. By moving shafts 9 and 10 independently by different distances in their axial directions, the planes in patient 3, whose images will be formed, are determined. Driving mechanism 11 is controlled by control circuit 14, and drives shafts 9 and 10. Control circuit 14 operates in accordance with the commands which an operator (or a doctor) has input by operating console 13. Shafts 9 and 10 and driving mechanism 11 can be replaced by an articulated robot.

Figure 3A:
FIGS. 3A to 3F are timing charts explaining the operation of the calculus disintegrator shown in FIG. 1.

Ultrasonic beam emitters 6A to 6G and ultrasonic transducers 7A and 7B are connected by cable 12 to driver 15, transmitters 17A and 17B and receivers 18A and 18B. Driver 15 is controlled by control circuit 14, thereby supplying high-level drive pulses 31, whose waveform is shown in FIG. 3A, to ultrasonic beam emitters 6A to 6G. The frequency at which to generate pulses 31 is determined by a command which the operator has input by operating console 13. In response to the drive pulses 31, beam emitters 6A to 6G emit ultrasonic beams having an intensity great enough to disintegrate calculus P.

Figure 3B:
Figure 3C:
Figure 3D:
Figure 3E:
Figure 3F:

Control circuit 14 supplies timing signals 32 and 33, whose waveforms are shown in FIGS. 3B and 3C, to transmitters 17A and 17B, respectively. Rate pulse generator 16 supplies rate pulses 34, shown in FIG. 3D, to transmitters 17A and 17B. As is evident from FIG. 3B, timing signal 32 is a train of pulses having a pulse width substantially equal to the interval between any two adjacent drive pulses 31. As is evident from FIG. 3C, timing signal 33 is also a train of pulses having a pulse with substantially equal to the interval between any two adjacent drive pulses 31, and is delayed by a period equal to the sum of its pulse width and the width of drive pulse 31, with respect to timing signal 32. Transmitters 17A generates drive pulses 35 at the same frequency as rate pulses 34 have been generated, during the period timing signal 32 remains at the high level. Similarly, transmitters 17B generates drive pulses 36 at the same frequency as rate pulses 34 have been generated, during the period timing signal 33 remains at the high level. Drive pulses 35, which are shown in FIG. 3E, are supplied to ultrasonic transducer 7A. Drive pulses 36, which are shown in FIG. 3F, are supplied to ultrasonic transducer 7B. Each of drive pulses 35 is actually a train of segmentary pulses for driving the piezoelectric elements of transducer 7A, respectively. Likewise, each of drive pulses 36 is actually a train of segmentary pulses for driving the piezoelectric elements of transducer 7B, respectively. These segmentary pulses are output from transmitters 17A and 17B at predetermined time intervals. Transducers 7A and 7B are driven by drive pulses 35 and 36, thus performing a sector scanning or a linear scanning on the ROI of patient 3. Ultrasonic echoes, which have resulted from the scanning, are emitted from the ROI. Transducers 7A and 7B detect the ultrasonic echoes, and convert them into echo signals 37 and 38. Echo signals 37 are supplied through cable 12 to receiver 18A, and echo signals 38 are supplied also through cable 12 to receiver 18B. From these echo signals, two B-mode tomograms will be formed.

Figure 4A:
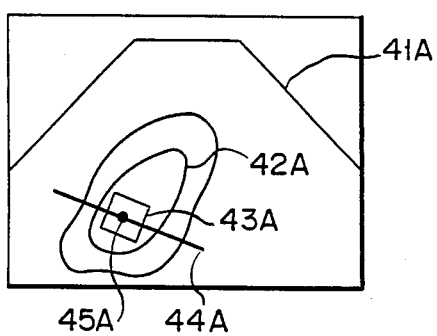
FIGS. 4A and 4B show the images displayed by the display device used in the calculus disintegrator of FIG. 1.
Figure 4B:
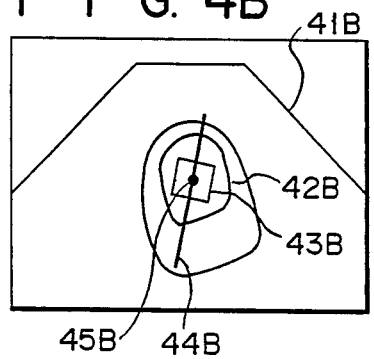

Receiver 18A detects and amplifies echo signals 37 and receiver 18B detects and amplifies echo signals 38. The output signals of receiver 18A are input to digital scan converter (DSC) 19A, and those of receiver 18B are input to digital scan converter (DSC) 19B. DSCs 19A and 19B are of the type commonly used in the ultrasonic diagnosis apparatuses. Each of them comprises an A/D converter for converting input analog signals to digital signals, a video memory for storing the digital signals as video data, and a D/A converter for converting the output of the video memory to analog signals. DSC 19A converts the output signals of receiver 18A to video signals which can be used by display 21A (or a video monitor). Similarly, DSC 19B converts the output signals of receiver 18A to video signals which can be used by display 21B (or a video monitor). Since receivers 18A and 18B intermittently output signals, DSCs 19A and 19B keep storing the video signals in their respective video memories while no signals are being supplied from receivers 18A and 18B. Upon receipt of the video signals from DSCs 19A and 19B, displays 21A and 21B displays tomograms 41A and 41B which, as is shown in FIGS. 4A and 4B, include images of the kidney containing calculus. In this embodiment, both ultrasonic transducers 7A and 7B perform a sector scanning on the ROI of patient 3. Therefore, tomograms 41A and 41B are shaped like a sector.

Position data signals 39, representing the position of applicator 4, are supplied to DSCs 19A and 19B from control circuit 14. Further, marker signals are input to DSCs 19A and 19B from marker generator 20. Position data signals 39 form data representing the position of the center of a region in which the ultrasonic beams emitted from beam emitters 6A to 6B are focused, and also data representing the positions of two selected planes in patient 3 of which tomograms 41A and 41B are formed from the echo signals output by ultrasonic transducers 7A and 7B. Control circuit 14 generates these pieces of position data in accordance with the way how driving mechanism 11 has driven applicator 4. Marker generator 20 generates a first marker signal based on the position data representing the center of the region in which the beams are focused. It also generates a second marker signal based on the position data representing the positions of the selected planes. The first marker signal represents a first marker, a square box indicating that region, and the second marker signal represents a second marker, i.e., the intersection line of the selected planes intersect with each other. DSCs 19A and 19B receive both the first marker signal and the second marker signal from marker generator 20. They supply the first and second marker signals to displays 21A and 21B. Display 21A displays first marker 43A (i.e., a square box) and second marker 44A (i.e., a line), both being superposed on tomogram 41A, as is shown in FIG. 4A. Display 21B displays first marker 43B (i.e., a square box) and second marker 44B (i.e., a line), both being superposed on tomogram 41B, as is shown in FIG. 4B. Since the line, along which the selected planes in patient 3 intersect, passes through the region in which the beams emitted from beam emitters 6A to 6G are focused, first and second markers 43A and 44A are superposed, one upon the other. For the same reason, first and second markers 43B and 44B are superposed, one upon the other. As is shown in FIGS. 4A and 4B, displays 21A and 21B also display images 45A and 45B of calculus P in the form of bright points.

It will now be described how to position applicator 4 such that the ultrasonic beams emitted from ultrasonic beam emitters 6A to 6G are focused on calculus P. First, the operator operates console 13, thereby moving applicator 4 until the image of the kidney appears in tomogram 41A or 41B displayed by display 21A or 21B. When applicator 4 is thus moved, its beam-emitting surface faces the kidney of patient 3. Assume that image 45A appears in tomogram 41A. This done, the operator operates console 13, thereby moving applicator 4 until the image 45A of calculus P appears on second marker 44A. More specifically, he or she operates two keys provided on console 13. When the first key is pushed, applicator 4 is moved in the direction parallel to the first selected plane in patient 3. When the second key is pushed, applicator 4 is moved in the direction parallel to the second selected plane in patient 3. When image 45A is superposed on second marker 44A shown in tomogram 41A, image 45B is automatically superposed on second marker 44B shown in the other tomogram 41B.

Then, the operator operates console 13, thereby move applicator 4 such that images 45A and 45B are moved on second markers 44A and 44B toward first markers 43A and 43B, respectively. More specifically, he or she operates two keys which are provided on console 13 in order to move applicator 4 in one direction and the other along the line along which the selected planes in patient 3 intersect with each other. When the operator operates these keys, thus images 45A and 45B of calculus P are moved in first markers 43A and 43B, respectively, the positioning of applicator 4 is completed.

After applicator 4 has been thus positioned, the operator pushes the button provided on console 13 in order to crush calculus P. Upon depression of this button, control circuit 14 supplies a timing signal to driver 15. Driver 15 supplies drive pulses 31 through cable 12 to ultrasonic beam emitters 6A to 6G. In response to these drive pulses, beam emitters 6A to 6G emit intense ultrasonic beams. Since applicator 4 has been properly positioned, the beams emitted from beam emitters 6A to 6G are applied onto calculus P, thereby giving mechanical impacts to calculus P. As these mechanical impacts are applied to calculus P one after another, calculus P is gradually disintegrated.

When patient 3 or applicator 4 moves during the calculus-disintegrating process, the positional relationship of calculus P and the beam-focassing point changes. As a result, the positional relationship of first marker 43A and image 45A, both displayed by display 21A, changes, and so does the positional relationship of first marker 43B and image 45B, both displayed by display 21B. In this case, the operator operates console 13 to set applicator 4 in such a position that the beams emitted from ultrasonic beam emitters 6A to 6G are focused on calculus P.

Calculus P has its shape changed every time it is disintegrated by a mechanical impact. Hence, its images 45A and 45B displayed by displays 21A and 21B also change in shape. Since the images 45A and 45B are taken in two planes intersecting with each other, the operator or doctor can visualize, from these images, a stereoscopic image of calculus P, and can therefore correctly understand how far the calculus-disintegrating has proceeded.

Figure 5:
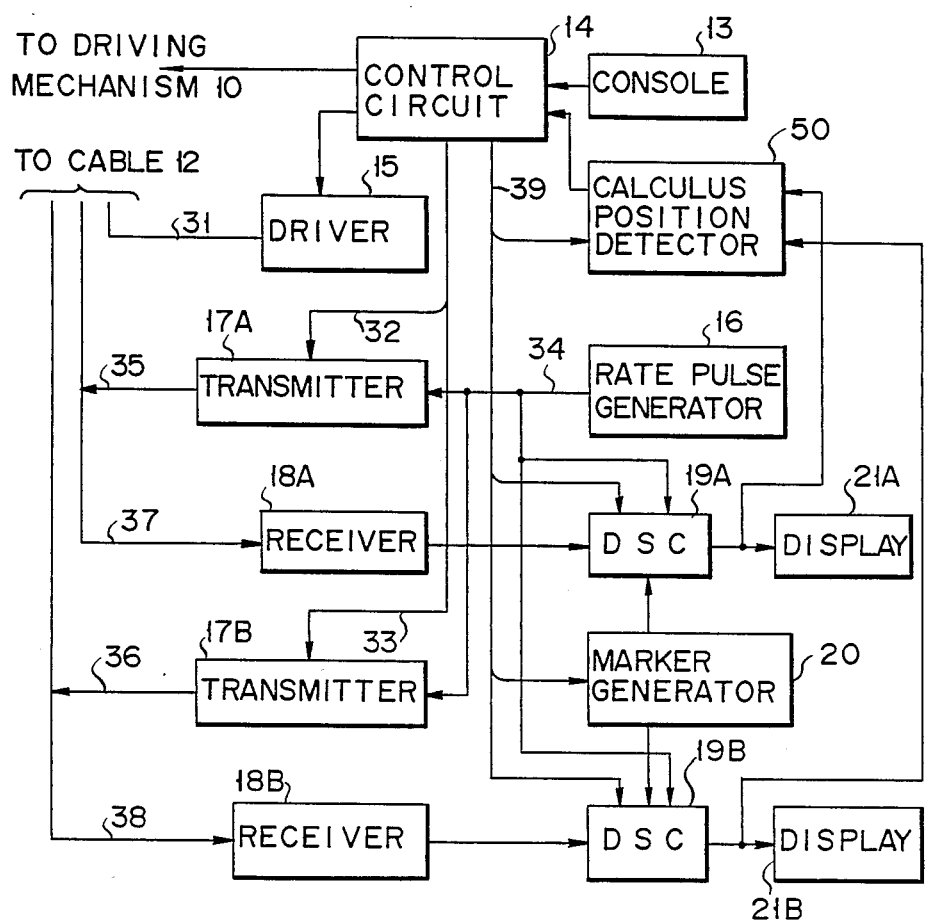
FIG. 5 is a block diagram of the electronic circuit of another embodiment of the present invention.

FIG. 5 shows a second embodiment of this invention. This embodiment is identical to the first embodiment of FIG. 1, except that detector 50 for detecting the position of calculus P is provided. Detector 50 receives data prepresenting the position of the region in which the beams from beam emitters 6A to 6G are focused, and contained in the position data signals 39 supplied from control circuit 14. It also receives the video signals supplied from DSCs 19A and 19B. From the input data and input signals, detector 50 detects the position of calculus P, more precisely, the distance between calculus P and the beam-focussing region and the direction in which calculus P is deviated from this point. Those components of the video signals supplied from DSCs 19A and 19B, which form the image of calculus P, are at levels higher than the other components of the video signals. Therefore, they can be readily detected by detector 50, whereby the position of calculus P can easily be determined. Detector 50 provides data showing the position of calculus. This position data is is supplied to control circuit 14. Circuit 14 controls, based on the position data, driving mechanism 11 in such manner that the images of calculus P come into square marks, i.e., second markers 43A and 43B (FIGS. 4A and 4B). In other words, applicator 4 is automatically positioned.

FIG. 6 shows a third embodiment of this invention. In this embodiment, tank 62 with an open top, filled with water, is located below bed 61 on which patient 3 lies to receive treatment. Applicator 4 is provided within tank 62. The open top of tank 62 is covered with membrane 63 which can pass ultrasonic waves but not water. It is desirable that membrane 63 be made of a material whose acoustic impedance is similar to those of water and human body. The third embodiment is advantageous in that patient 3 can receive treatment, while he or she is taking a comfortable position.

The present invention is not limited to the embodiments described above. Various changes and modifications can be made, without departing from the spirit and scope of the invention. All embodiments described above are calculus-disintegrators. Nonetheless, this invention can apply to hyperthemia treatment systems for healing cancers by applying ultrasonic beams to the cancers.

What is claimed is:

1. An ultrasound therapy apparatus for a treating of an object within a patient, said apparatus comprising:
    at least one ultrasonic beam emitter means for emitting an ultrasonic beam onto the object;
    at least two ultrasonic transducer means for applying ultrasonic beams to the patient, and detecting ultrasonic echoes coming from the patient;
    support means supporting said ultrasonic beam emitter and said ultrasonic transducers in a specific positional relationship;
    means for mechanically driving said support means such that the beam emitted from said ultrasonic beam emitter means is focused at a given position within the patient;
    means for supplying drive signals to said ultrasonic beam emitter means;
    signal-receiving means for receiving echo signals corresponding to the ultrasonic echoes detected by said ultrasonic transducer means;
    means for forming first and second tomograms in accordance with the echo signals supplied from said signal-receiving means, each tomogram being of a selected plane of the patient, one plane intersecting with the other on a line which passes through a region in which the beam emitted by said ultrasonic beam emitter means is focused; and
    display means for displaying the first and second tomograms, for displaying first markers indicating a region in which the ultrasonic beam emitted by said ultrasonic beam emitter means is focused and being superposed on the first and second tomograms, and for displaying second markers representing the intersecting line of the two planes and being superposed on the first and second tomograms.

2. An ultrasound therapy apparatus according to claim 1, further comprising a bathtub in which the patient sits in order to receive treatment, and which contains said support means.

3. An ultrasound therapy apparatus according to claim 1, further comprising:
    a bed on which the patient lies to receive treatment and which contains said support means;
    a tank located below said bed and having an open top; and
    a membrane covering said open top and made of a material able to pass ultrasonic waves but not water.

4. An ultrasound therapy apparatus according to claim 1, wherein said ultrasonic beam emitter means is provided in a predetermined region of said support means, and said ultrasonic transducer means are provided outside this region.

5. An ultrasound therapy apparatus according to claim 1, wherein each of said ultrasonic transducer means comprises an array of piezoelectric elements, whereby the ultrasonic beam emitted from the ultrasonic transducer means scans a region of interest within the patient.

6. An ultrasound therapy apparatus according to claim 1, further comprising means for detecting the position of the object on the basis of said echo signals, and means for controlling said means for mechanically driving the support means in such a manner that said region, in which the ultrasonic beam is focused, is positioned at the object.

* * * * *